(12) United States Patent
Keller et al.

(10) Patent No.: US 12,127,871 B2
(45) Date of Patent: Oct. 29, 2024

(54) COOLING SYSTEM WITH SOLID MATERIAL HEATSINK FOR A DIAGNOSTIC MEDICAL IMAGING APPARATUS

(71) Applicant: Siemens Medical Solutions USA, Inc., Malvern, PA (US)

(72) Inventors: John Keller, Knoxville, TN (US); James L. Corbeil, Knoxville, TN (US); Ziad Burbar, Knoxville, TN (US); Stefan Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 210 days.

(21) Appl. No.: 18/000,861

(22) PCT Filed: Jul. 20, 2020

(86) PCT No.: PCT/US2020/070297
§ 371 (c)(1),
(2) Date: Dec. 6, 2022

(87) PCT Pub. No.: WO2022/019954
PCT Pub. Date: Jan. 27, 2022

(65) Prior Publication Data
US 2023/0210486 A1    Jul. 6, 2023

(51) Int. Cl.
*A61B 6/00* (2024.01)
(52) U.S. Cl.
CPC .................. *A61B 6/4488* (2013.01)
(58) Field of Classification Search
CPC ........ A61B 6/4488; A61B 6/032; A61B 6/037
See application file for complete search history.

(56) References Cited

U.S. PATENT DOCUMENTS

| | | | |
|---|---|---|---|
| 5,444,752 A * | 8/1995 | Dobbs | G21K 5/04 378/19 |
| 5,610,968 A | 3/1997 | Deucher et al. | |
| 6,511,224 B1 | 1/2003 | Lu et al. | |
| 6,988,827 B2 | 1/2006 | Mueller | |
| 8,590,331 B2 | 11/2013 | Corbeil et al. | |
| 10,178,976 B2 | 1/2019 | Liu et al. | |
| 2013/0119259 A1 | 5/2013 | Martin | |
| 2019/0298286 A1 | 3/2019 | Kuehn et al. | |

(Continued)

FOREIGN PATENT DOCUMENTS

| | | |
|---|---|---|
| CN | 106901772 | 6/2017 |
| CN | 109589124 | 4/2019 |

(Continued)

OTHER PUBLICATIONS

Beach, Paige, "Laird's Liquid Cooling Systems Increase Medical Imaging Equipment Uptime", Oct. 31, 2017, 12 pages, https://www.designworldonline.com/lairds-liquid-cooling-systems-increase-medical-imaging-equipment-uptime/.

(Continued)

*Primary Examiner* — Kiho Kim (57) ABSTRACT

A gantry cooling system of a diagnostic medical imaging apparatus transfers apparatus-generated heat, such as gantry heat, to a solid material heatsink, via a circulating-fluid coolant conduit. In some embodiments, the heatsink is incorporated in the ground or within the building structure housing the apparatus.

17 Claims, 3 Drawing Sheets

(56) References Cited

U.S. PATENT DOCUMENTS

2019/0306964 A1    3/2019  Rogers et al.
2020/0100742 A1    4/2020  Mueller et al.

FOREIGN PATENT DOCUMENTS

EP         404335      12/1990
JP        2008164548    7/2008

OTHER PUBLICATIONS

Ducharme, Greg, How to Cool X-rays in Industrial Scanners, Industrial Equipment News (IEN), Mar. 6, 2018, 5 Pages, https://www.ien.com/product-development/article/20995123/xray-cooling-in-industrial-scanners.

"Liquid Cooling Options for PET and SPECT Scanners", Laird Thermal Systems (2019), 6 pages, https://www.lairdthermal.com/resources/applicationnotes/liquid-cooling-options-pet-and-spect-scanners.

"Liquid Cooling Options for PET and SPECTScanners", Laird Thermal Systems Application Note, Sep. 2017, 9 pages.

"Next-generation heat pump offers more affordable heating and cooling", (Jun. 21, 2018), retrieved Feb. 5, 2020, 2 pages, https://phys.org/news/2018-06-next-generationcooling.html.

"Types of Radiant Cooling Systems", homepage (http://www.oorja.in/); radiant cooling (http://www.oorja.in/what-is-radiantcooling/); 8 pages.

International Search Report for Corresponding PCT Application No. PCT/US2020/070297, dated Mar. 25, 2021.

* cited by examiner

COOLING SYSTEM WITH SOLID MATERIAL HEATSINK FOR A DIAGNOSTIC MEDICAL IMAGING APPARATUS

TECHNICAL FIELD

A cooling system for a diagnostic medical imaging apparatus. More particularly, a gantry cooling system that circulates fluid coolant between the gantry and a solid material heatsink.

BACKGROUND

Diagnostic medical imaging apparatuses include, by way of non-limiting example computed tomography (CT), two-dimensional digital radiography (DR), positron emission tomography (PET), magnetic resonance imaging (MRI), PET/CT, and PET/MRI modalities. Many of these imaging apparatuses or systems include a toroidal-shaped gantry structure through which is inserted a patient table. The gantry includes one or more electromagnetic radiation detectors, which emit electrons in response to incident photons of electromagnetic radiation. In some modalities, the incident photons are transmitted X-rays or ionized radiation emissions at the higher end of the electromagnetic frequency range, while in other modalities the incident photons are within the radio frequency range. The output electrons of the detector are processed by detector electronics to generate detector output signals, which are subsequently processed by the imaging apparatus to generate patient images. Exemplary electromagnetic radiation detectors include photomultiplier tubes (PMTs) and silicon photomultipliers (SiPMs). Detector electronic packages are often housed with the detectors within the gantry structure. In order to generate usable patient image information during a patient scan, the detectors and detector electronic packages are maintained within relatively narrow temperature fluctuation and operational temperature bandwidths. Exceeding the desired temperature fluctuations and operational temperature bandwidths may result in inaccurate detector readings and/or excessive noise generation components in the readings, leading to a poorer quality set of patient images.

During and between patient scans, gantries and other components of imaging systems generate cyclic, fluctuating heat. In order to maintain detectors and detector electronics within desired temperature bandwidths, heat generated within the gantry structure is transferred out of the gantry. Known gantry cooling systems for medical imaging apparatuses typically transfer heat from the gantry into the ambient air of the imaging room, resulting in spikes of increased room temperature during and after a patient scan. The increasing imaging room temperature is uncomfortable for patients and medical technicians in the room, often requiring use of air conditioning systems to cool the room. Sporadically increasing ambient room temperature through sequentially scheduled patient scans over the course of the day also raises internal gantry temperature—potentially raising the internal gantry temperature above the desired detector operating temperature bandwidth.

SUMMARY

Exemplary embodiments described herein transfer imaging apparatus generated heat, including gantry heat, to solid material heatsinks, by circulating fluid in coolant lines passing through the gantry and the heatsink. The solid material heatsinks have relatively large, steady-state heat capacitance, capable of absorbing cycles of transient heat generated during one or more patient imaging scans. In some embodiments, the heatsinks are coupled to the medical imaging apparatus, or are located remote the apparatus, in building structure within or outside of the imaging room that houses the imaging apparatus. In some embodiments, the heatsinks are incorporated directly within the building structure, or in ground. Heatsinks integral with the building structural floor, walls, ceiling of the imaging room save floor space in the imaging room. Transferring gantry or other apparatus generated heat to thermal mass of a solid material heatsink, by circulating coolant fluid within the fluid coolant lines, reduces waste heat that would otherwise raise ambient temperature of the imaging room during any individual patent scan. In some embodiments, the only energy required to transfer gantry heat to the solid heat sink is for operation of a low pressure, coolant circulating pump. In some embodiments, the gantry waste heat is recycled to reduce total energy use of the building structure housing the medical imaging apparatus. For example, in some embodiments, heat retained within the heatsink is utilized for steady-state, passive heating of the imaging room. In other embodiments, heat retained within the heatsink is subsequently used by building environmental control systems (e.g., HVAC systems) and/or domestic hot water heating systems.

Exemplary embodiments feature a cooling system for a gantry of a diagnostic medical imaging apparatus that is oriented in an imaging room of a building structure. Diagnostic medical imaging apparatuses include, by way of non-limiting example computed tomography (CT), two-dimensional digital radiography (DR), positron emission tomography (PET), magnetic resonance imaging (MRI), PET/CT, and PET/MRI modalities. The imaging apparatuses or systems respectively include a gantry structure, having therein one or more electromagnetic radiation detectors and a first coolant passage for absorption of heat generated within the gantry. The gantry includes one or more electromagnetic radiation detectors, which emit electrons in response to incident photons of electromagnetic radiation. In some modalities, the incident photons are transmitted X-rays or ionized radiation emissions at the higher end of the electromagnetic frequency range, while in other modalities the incident photons are within the radio frequency range. A solid material heatsink, having enough thermal mass to receive and absorb all heat generated within the gantry, is oriented external the gantry. The heatsink defines a second coolant passage. A coolant fluid conduit couples the first and second coolant passages in at least one closed fluid loop. A coolant fluid circulates within the at least one closed fluid loop of the coolant fluid conduit, for transferring heat generated within the gantry from the first coolant passage to the second coolant passage defined within the heat sink. The second coolant passage transfers the gantry heat from the coolant fluid to the heatsink by thermal conduction.

Other exemplary embodiments feature a method for cooling a gantry of a diagnostic medical imaging apparatus, by orienting a medical imaging apparatus in an imaging room of building structure. The medical imaging apparatus has a gantry, which includes therein at least one electromagnetic radiation detector and a first coolant passage for absorption of heat generated within the gantry. A solid material heatsink is oriented external the gantry. The heatsink has enough thermal mass to receive and absorb all heat generated within the gantry. The heatsink defines a second coolant passage. The first and second coolant passages are coupled in at least one closed fluid loop, with a coolant fluid conduit. Coolant fluid is circulated within the coolant fluid conduit, for transferring heat generated within the gantry from the first coolant passage to the second coolant passage defined within the heatsink. The second coolant passage transfers the gantry heat from the coolant fluid to the heatsink by thermal conduction.

The respective features of the exemplary embodiments that are described herein are applied jointly or severally in any combination or sub-combination.

BRIEF DESCRIPTION OF DRAWINGS

The exemplary embodiments are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Exemplary embodiments are utilized in a gantry cooling system of a diagnostic medical imaging apparatus, which transfers gantry heat and other apparatus generated heat to a solid material heatsink, via a circulating-fluid coolant conduit. The solid material heatsink has enough thermal mass to receive and absorb all heat generated within the gantry. In some exemplary embodiments, the heatsink is a slab of concrete, with embedded coolant conduit loops, located in the ground or within the building structure housing the apparatus. In other exemplary embodiments, the heat sink is a structural building panel, with embedded coolant conduit loops, used to form walls, floors, and/or ceilings of an imaging room that houses the medical imaging apparatus. Advantageously, in some embodiments, gantry heat transferred to and retained within the heatsink is released into the building structure's ambient air by convection, for energy-efficient passive heating, or as a regenerative heat source for the building's HVAC environmental control system and/or domestic hot water heating system. Some embodiments of the heatsink are retrofitted to existing types of gantry cooling systems, including those in the field already incorporating air-fluid or fluid-fluid heat exchangers. Other embodiments of the heatsink are incorporated into revised designs of gantry cooling systems, in newly manufactured medical imaging apparatuses. Some embodiments of the solid material heatsink are coupled directly to the medical imaging apparatus.

Exemplary cooling system embodiments described herein reduce detector and/or detector electronics package temperature fluctuations to less than 1 degree Celsius (1° C.) within a single patient imaging scan and temperature variation bandwidth among a plurality of sequential patient scans within six degrees Celsius (6° C.), to generate usable patient image information. In other embodiments, the cooling systems reduce detector and/or detector electronics package temperature fluctuations to less than one-half degree Celsius (0.5° C.) within a single patient imaging scan and temperature variation bandwidth among a plurality of sequential patient scans within two degrees Celsius (2° C.)

Figure 1:
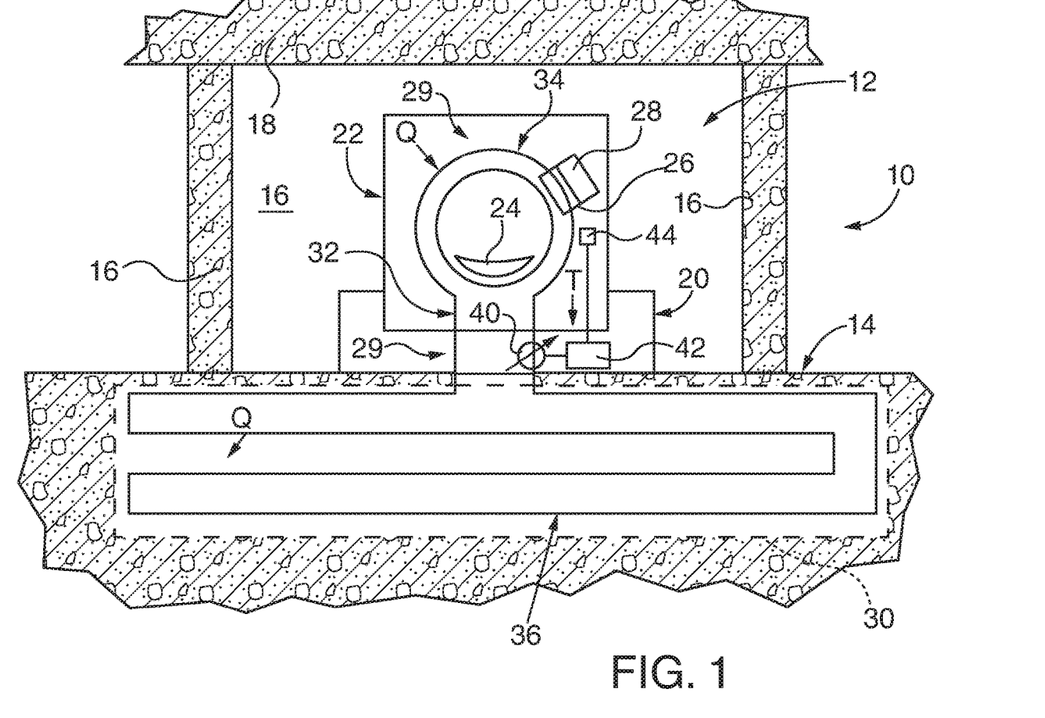
FIG. 1 is a schematic view of a diagnostic medical imaging apparatus and gantry cooling system, with a heatsink embedded within a floor of an imaging room of a building structure.

FIG. 1 shows a building structure 10, including an imaging room 12 with a floor 14, walls 16 and a ceiling 18; typically constructed of concrete or other dense material for structural support and electromagnetic isolation within the room. A medical imaging apparatus 20, such as a PET scanner, includes a gantry 22 with a toroidal central bore circumscribing a patient table 24. The gantry 22 houses one or more electromagnetic radiation detectors 26 and one or more electronics packages 28, with only one of each shown for illustrative purposes. Heat Q is generated within the gantry 22 during scanner operation, which will otherwise raise internal temperature of the imaging apparatus, as well as the ambient temperature of the imaging room 12. A gantry cooling system 29 transfers the heat Q from the gantry 22 to a heatsink 30, comprising a solid thermal mass, via a coolant fluid conduit 32. The coolant fluid conduit 32 is a fluid loop, comprising a first coolant passage 34, shown as a coolant pipe for illustrative purposes, in the gantry 22 and a second coolant fluid passage 36, shown as a serpentine coolant pipe loop for illustrative purposes, embedded in the heatsink 30. Either of the types of first 34 or second 36 coolant passages are selectively constructed to exchange heat with fluid coolant, including by way of nonlimiting example any one or more of finned or non-finned heat plates, tubing, fluid-fluid heat exchangers, air-fluid heat exchangers, embedded cooling passages within components, condensers, and evaporators. While the embodiment of FIG. 1 has a single continuous coolant fluid conduit 32, other embodiments comprise plural fluid conduits, including parallel or series cooling loop and/or subloops in fluid communication with the coolant fluid conduit.

A variable-speed circulating pump 40 circulates coolant fluid within the coolant fluid conduit 32. A thermal controller 42 selectively varies flow rate of the circulating pump 40 at least partially based on temperature T, sensed by a temperature sensor 44 in the gantry 22. In some embodiments, the thermal controller 42 is in a feedback loop with the temperature sensor 44, to maintain gantry operational temperature within a defined bandwidth during imaging apparatus 20 operation over plural patient imaging scans and to maintain a defined temperature fluctuation parameters within any individual imaging scan. In some embodiments, there is no thermal controller or temperature sensor: the circulating pump is a non-variable speed pump or alternatively, a variable-speed pump operated at a designated flow rate. In some embodiments, there is no circulating pump; coolant fluid circulates only by thermal convection. In embodiments where the coolant fluid conduit comprises multiple subloops and/or branches, circulating pumps are selectively incorporated in one or more of them: with or without a thermal controller and/or a temperature sensor.

In FIG. 1, the variable-speed circulating pump 40 circulates coolant fluid within the coolant fluid conduit 32, which transfers heat Q generated within the gantry 22 from the coolant pipe of the first coolant passage 34 to the serpentine coolant pipe loop of the second coolant passage 36, defined within the heatsink 30. The solid material forming the heatsink is concrete, which also forms the floor 14 of the imaging room 12.

When building a new imaging room 12, the serpentine coolant pipe loop or any other desired fluid conduit pattern of the second coolant passage 36 is easily embedded into a newly poured concrete floor slab 14, or walls 16 or ceiling 18. Concrete is often utilized in new imaging room 12 construction for its excellent electromagnetic energy isolation properties. Concrete has a relatively high thermal capacitance, $C_p$, of approximately 0.88 kilo-Joules/Kg-° C. As will be described in modeling below, a heatsink comprising a concrete floor slab, roughly approximating the floor space of a typical imaging room has sufficient thermal mass to absorb all gantry heat generated during a typical eight hour work shift, while only warming the floor less than thirteen degrees Celsius. The concrete floor slab radiates heat back to the imaging room relatively slowly, which advantageously allows patients and imaging staff to walk comfortably on a warm floor during work shifts, and helps maintain the imaging room at a more comfortable ambient temperature between work shifts.

Figure 2:
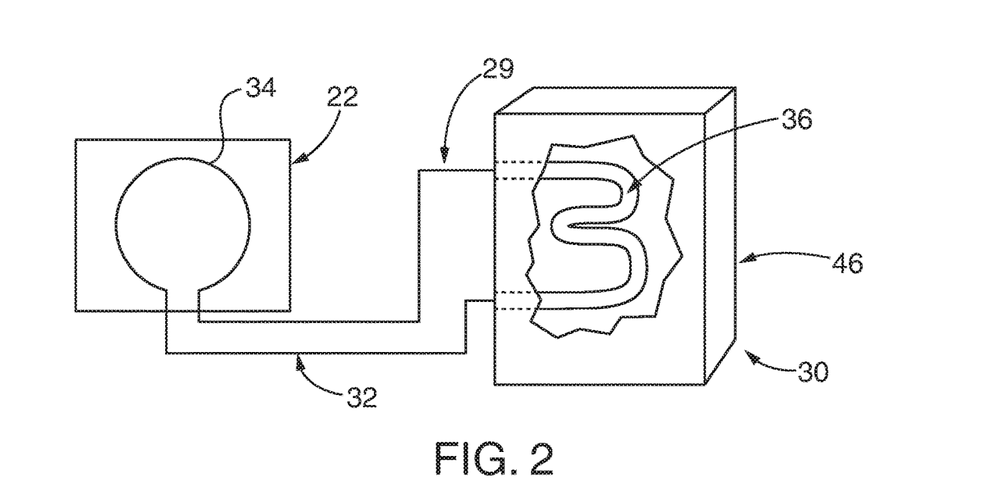
FIG. 2 is a schematic view of another embodiment of a diagnostic medical imaging apparatus and gantry cooling system, with a heatsink embedded within a modular building panel of a building structure.

Referring to FIG. 2, modular panels 46, (e.g., concrete, metal, or other solid building material), comprise the heatsink 30. The modular panels 46 provide a useful alternative to poured-in-place, heatsinks, when a new or remodeled imaging room is constructed with prefabricated panels. A serpentine coolant pipe loop comprises the second coolant fluid passage 36, which is embedded or otherwise coupled to the modular panel 46, to form the heatsink 30. The modular panels 46 are used to form imaging room ceilings, walls, and/or floors. In some embodiments, one or more modular panels 46 are laid over an existing building floor or affixed to existing walls or ceiling. One or more modular panels 46 are coupled to the coolant fluid conduit 32 and the first coolant passage 34 of the gantry, in a continuous loop or a plurality of branched loops, to complete the cooling system 29. In some embodiments, the modular panel 46 is coupled directly to the medical imaging apparatus, rather than being integrated or otherwise coupled to the imaging room's building structure or other portion of the building.

Figure 3:
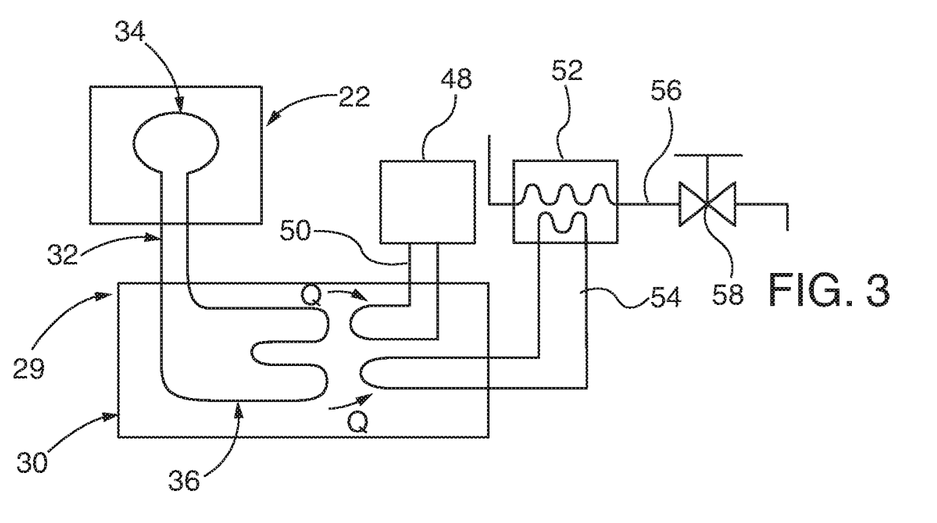
FIG. 3 is a schematic view of another embodiment of a diagnostic medical imaging apparatus and gantry cooling system, with a heatsink transferring gantry heat to respective environmental control systems (e.g., HVAC) and domestic hot water heating systems of a building structure.

In FIG. 3, the gantry cooling system 29 waste heat generated within the gantry 22 and stored within the heatsink 30 heats the building structure's environmental control system and/or domestic hot water system. Specifically, the coolant fluid conduit 32 transfers gantry heat absorbed by the first coolant passage 34 to the second coolant passage 36 of the heatsink 30. Heat Q within the heatsink 30 flows to the building's HVAC system 48 via an HVAC coolant loop 50 and flows to the building's domestic hot water system through the hot-water heat exchanger 52 via a hot-water feed loop 54. Heated domestic water feeds through hot water line 56, for example to a faucet or tap 58.

Figure 4:
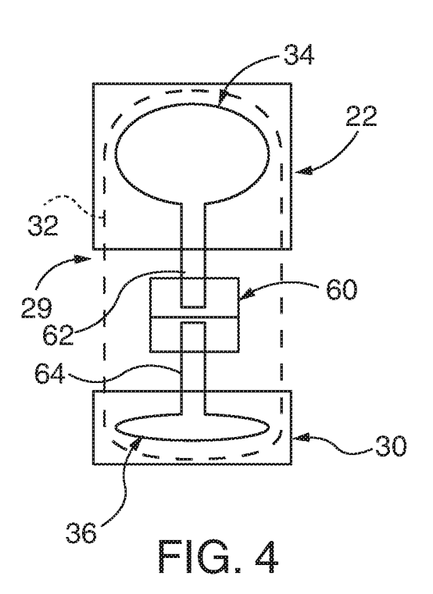
FIG. 4 is a schematic view of another embodiment of a diagnostic medical imaging apparatus and gantry cooling system, with a fluid-fluid heat exchanger interposed between a coolant loop within the gantry and a coolant loop within the heatsink.

The gantry cooling system 29 of FIG. 4 interposes a fluid-fluid heat exchanger 60 in the coolant fluid conduit 32, between the first coolant passage 34 of the gantry 22 and the second coolant passage 36 of the heatsink 30. In some embodiments, the heat exchanger 60 is oriented in the gantry 22. In other embodiments, the heat exchanger 60 is oriented elsewhere in the medical imaging apparatus or in a remote location inside or outside of the imaging room. A first coolant conduit subloop 62 transfers heat from the gantry 22 to the heat exchanger 60. The gantry heat in turn is transferred in a second coolant conduit subloop 64 to the heatsink 30. Advantageously, the embodiment of FIG. 4 facilitates retrofitting of the heatsink 30 to an existing design fluid-fluid gantry cooling system in an existing imaging system design—whether for an existing apparatus or for a newly manufactured apparatus.

Figure 5:
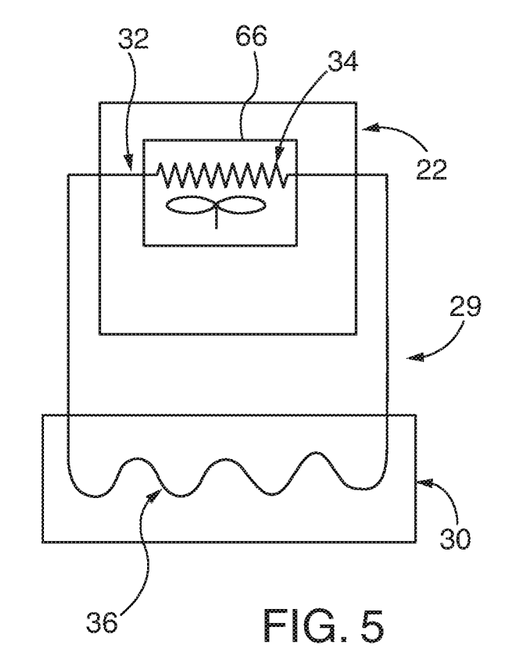
FIG. 5 is a schematic view of another embodiment of a diagnostic medical imaging apparatus and gantry cooling system, with an air-fluid heat exchanger in the gantry coolant loop.

The gantry cooling system 29 of FIG. 5 utilizes an air-fluid heat exchanger 66 in the gantry 22. Cooling air is circulated within the gantry 22, passing over the coolant-filled tubes in the heat exchanger 66 that form the first coolant passage 34. Coolant fluid in the coolant fluid conduit 32 circulates between the air-fluid heat exchanger 66 and the second coolant passage 36 of the heatsink 30. Advantageously the embodiment of FIG. 5 facilitates retrofitting of the heatsink 30 to an existing design air-fluid gantry cooling system in an existing imaging system design—whether for an existing apparatus or for a newly manufactured apparatus.

The gantry cooling systems of FIGS. 1-5 utilize known liquid and mixed phase liquid/gaseous coolant fluids, including by way of non-limiting example: glycol, water, water-glycol, oil, and ammonia. The cooling systems 29 described herein utilize any known type of coolant fluid used in medical imaging apparatuses.

Figure 6:
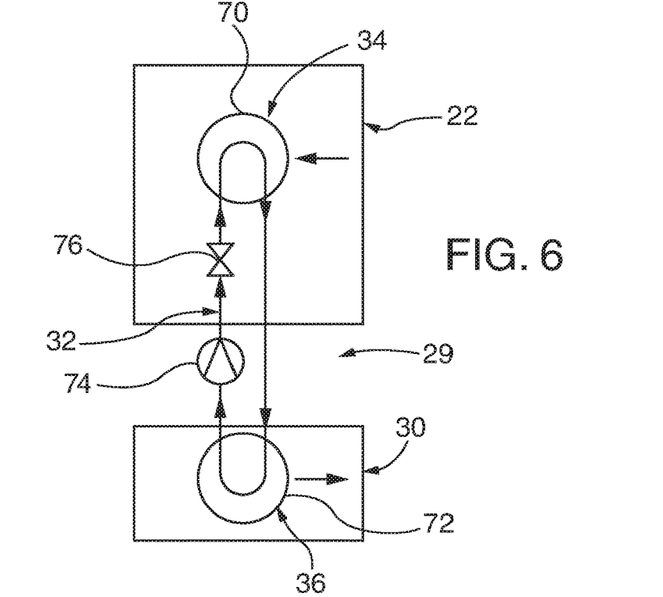
FIG. 6 is a schematic view of another embodiment of a diagnostic medical imaging apparatus and gantry cooling system, with a mixed-phase coolant loop between the gantry and the heatsink.

The cooling system embodiment of FIG. 6 incorporates a mixed-phase (i.e., liquid and gas mixture) coolant. Exemplary ammonia or chlorofluorocarbon coolant media are circulated within a coolant fluid conduit 32 between an evaporator 70 in the gantry 22 and a condenser 72 formed in the heatsink 30. Liquid coolant is compressed in a compressor or pump 74 into expansion valve 76, exiting as a gaseous coolant, which absorbs heat in the evaporator 70. The gaseous coolant re-condenses to liquid form in the condenser 72, transferring the gantry heat to the heatsink 30. The evaporator 70 and condenser 72 are shown schematically for illustrative purposes.

Figure 7:
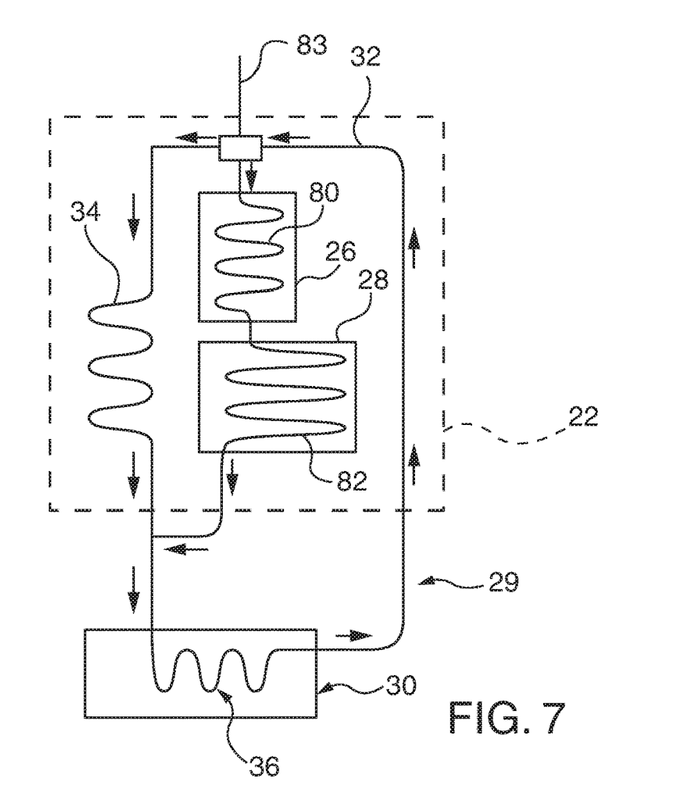
FIG. 7 is a schematic view of another embodiment of a diagnostic medical imaging apparatus and gantry cooling system, where the gantry coolant loop is incorporated within passages formed within the magnetic radiation detector and envelops an electronic package within the gantry.

In FIG. 7, the coolant fluid conduit 32 of the cooling system 29 incorporates a first coolant passage 34 for general gantry 22 cooling, and a branch or subloop comprising coolant passage 80 and a cooling pipe 82 of the first coolant passage, respectively for direct cooling and thermal isolation of the detector 26 and the electronics package 28 from the general ambient temperature within the gantry. For illustrative purposes, the gantry structure 22 is shown schematically in dashed lines. In this embodiment, the coolant passage 80 is integrated into the structure of the detector 26. The serpentine profile cooling pipe 82 abuts or otherwise is in direct thermal communication with one or more exterior surfaces of the electronics package 28. The coolant fluid branch 80 and 82 and the first coolant passage 34 off the coolant fluid conduit 32 are joined in a shared fluid manifold 83. In some embodiments, the fluid manifold includes coolant flow restrictors for varying coolant flow rates among the branches (not shown). In some embodiments comprising multiple parallel or branched cooling subloops of the first coolant passage 34 within the cooling system 29, each subloop can vary heat transfer rates, during initial design or by field adjustment, to draw heat out of the gantry 22 to the second coolant passages 36 of the heatsink 30 and/or to isolate thermal zones within the gantry from higher temperature regions within the gantry. For example, an electromagnetic radiation source (not shown) within a gantry generates heat during operation. In some embodiments that source will have a dedicated, isolated first coolant passage subloop, filled with a coolant (e.g., oil), having a higher vaporizing temperature than other coolants in the cooling system, with its own dedicated fluid-fluid heat exchanger in thermal communication with the fluid coolant conduit. In some embodiments, other subloops of first coolant passages function as thermal isolators, such as the branch or subloop coolant passage 80 and the cooling pipe 82 of FIG. 7 that isolates the detector 26 and the electronics package 28 from higher temperature zones in the gantry 22.

In the embodiment of FIG. 1, the cooling system 29 incorporates a thermal controller 42. In some embodiments, the thermal controller comprises digital electronic controller platform architecture and implementation by software modules executed by a computer processor. Exemplary embodiments of the thermal controller 42 are implemented in various forms of hardware, software, firmware, special purpose processors, or a combination thereof. Preferably, aspects of the embodiments are implemented in software as a program tangibly embodied on a program storage device. The program is uploaded to, and executed by, a machine comprising any suitable architecture. Preferably, the machine is implemented on a computer platform having hardware such as one or more central processing units (CPU), a random-access memory (RAM), and input/output (I/O) interface(s). The computer platform also includes an operating system and microinstruction code. The various coolant temperature sensing and fluid circulation processes and functions described herein are either part of the microinstruction code or part of the program (or combination thereof) which is executed via the operating system. In addition, various other peripheral devices may be connected to the computer/controller platform, such as the temperature sensor 44.

Solid material heatsinks, such as the heatsink 30 embodiments described herein, utilize relatively large thermal mass to absorb heat generated within the gantry, or other components of a medical imaging apparatus during patient imaging procedures scheduled throughout a day. Imaging apparatus heat generation tends to be sporadic in nature, with heating spikes occurring during individual patient scans, followed by non-heat generating quiescent periods. In known gantry cooling systems that release gantry heat into the imaging room, ambient air temperature of the room spikes proportionally during a patient scanning procedure. In the cooling system embodiments described herein, thermal mass of the heatsink is selected, based on anticipated heat generation cycles of the medical imaging apparatus, including its gantry, during a designated time interval, and ability of the heatsink to release the retained heat slowly enough not to raise ambient temperature of the scanning room and/or the scanning detectors and/or the electronic packages of the medical imaging apparatus beyond permissible limits. For example, a heatsink embedded within a concrete floor of an imaging room can be sized to absorb transient heating cycles of a gantry of a medical imaging apparatus and release that absorbed transient heat back into the ambient air of imaging room at a rate that is not uncomfortable to patients or medical personnel occupying the room.

Using the following example, a heatsink formed within a concrete slab of a medical imaging room's floor absorbs all heat energy (E) generated by a PET scanner injecting a continuous 3-kilowatt sustained waste heat load (Q) throughout total time (t) of an eight-hour shift of scheduled patient scans. The total generated heat energy (E) that can be absorbed by the concrete is approximately 86400 kilojoules. It is unlikely that any PET scanner would be in continuous use for an eight-hour period, as there are inherent delays preparing individual patients for periodically scheduled scans. It is also overly pessimistic to assume that the concrete floor absorbs and retains 100% of the PET scanner's waste heat (Q) over the entire eight-hour period. Thus, the following estimation of the concrete heatsink's temperature rise is a worst-case assumption for modeling purposes. Assuming that the concrete slab is 12 cm thick, with a surface area of approximately 26.5 m$^2$, the total volume (v) of concrete is approximately 3.18 m$^3$. With an approximate concrete density ($\rho$) of 2400 kg/m$^3$, the total mass (M) of the concrete slab is approximately 7645 kg. Heat capacitance of concrete ($C_p$) is approximately 0.88 kJ/kg-° C. Using the following formula, increase in temperature of the concrete ($\Delta T$), i.e., final temperature (Tf) after slab heating minus initial slab temperature (Ti), will be:

$$E = MC_p(\Delta T)$$

The concrete's temperature rise ($\Delta T$) is approximately 12.8° C. after absorbing the 86400-kJ heat energy load of the PET scanner, with the explicit assumption that the concrete heatsink retains all the heat load over the entire eight-hour shift. Assuming that prior to initiating the imaging scans at the beginning of the scanning shift the concrete floor's temperature was 18° C. (matching desired ambient temperature of the imaging room maintained by the building's HVAC system) and that the floor released no heat to its surroundings, floor temperature will rise 12.8° C. by the end of the scheduled eight hour shift, to an environmentally acceptable 30.8° C. The absorbed heat is released back into the scanning room, until the heated floor surface again matches the room's 18° C. ambient temperature achieved again.

The same general heat transfer objectives are achievable with other suitably sized solid material heatsinks—whether embedded within building structural components or the ground or formed as stand-alone components in the imaging room or coupled directly to the medical imaging apparatus. By way of another exemplary embodiment, an imaging scanner apparatus incorporates the solid material heatsink within a mass of a seismic plate or electromagnetic shield that is coupled to the apparatus.

In many embodiments, operational energy needed to cool the gantry with a solid material heatsink described herein is reduced compared to known gantry cooling systems that dump gantry heat directly into the ambient air of the imaging room, which often require use of combinations of relatively noisy powered compressors, chillers and forced air fan ducts. Some cooling system embodiments described herein rely on thermal convection to circulate coolant fluid between the gantry and the heatsink. Others rely on relatively low energy consumption fluid circulating pumps to circulate coolant fluid relatively quietly.

The cooling system embodiments, including the solid material heatsinks described herein, offer a broad range of potential individual benefits, including: low maintenance and operating energy consumption, simple construction, low noise, as well as narrower bandwidths of temperature fluctuation during individual imaging scans and narrower bandwidths of temperature range over a plurality of sequential imaging scans. The heatsink embodiments described herein are easily incorporated into other imaging apparatus components (e.g., seismic plates or radiation shields) and in the floor, walls and/or ceilings of the imaging room structure and the surrounding building structure.

Although various embodiments have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of "including", "comprising", "incorporating", or "having" and variations thereof herein is meant to encompass the items listed thereafter and equivalents thereof as well as additional items. Unless specified or limited otherwise, the terms "mounted", "connected", "supported", and "coupled" and variations thereof are to be interpreted broadly; they encompass direct and indirect mountings, connections, supports, and couplings. Further, "connected" and "coupled" are not restricted to physical, mechanical, or electrical connections or couplings.

What is claimed is:

1. A cooling system for a gantry of a diagnostic medical imaging apparatus, comprising:
   a medical imaging apparatus oriented in an imaging room of a building structure;
   a gantry of the medical imaging apparatus, having therein at least one electromagnetic radiation detector and a first coolant passage for absorption of heat generated within the gantry;
   a solid material heatsink, having a thermal mass that receives and absorbs all heat generated within the gantry, oriented external the gantry, the heatsink defining a second coolant passage;
   a coolant fluid conduit coupling the first and second coolant passages in at least one closed fluid loop; and
   coolant fluid circulating within the at least one closed fluid loop of the coolant fluid conduit, for transferring heat generated within the gantry from the first coolant passage to the second coolant passage defined within the heat sink, the second coolant passage transferring the gantry heat from the coolant fluid to the heatsink by thermal conduction.

2. The cooling system of claim 1, further comprising the solid material heatsink forming a structural element defining a wall or a floor or a ceiling of the building structure or buried underground, with the second coolant passage embedded therein.

3. The cooling system of claim 1, further comprising the solid material heatsink forming a modular building panel, with the second coolant passage embedded within the modular panel.

4. The cooling system of claim 3, the modular panel forming a structural element defining a wall or a floor or a ceiling of the building structure or buried underground.

5. The cooling system of claim 1, further comprising a fluid-to-fluid heat exchanger coupled to the fluid coolant conduit, interposed between the second coolant passage and an HVAC and/or domestic water heating system, for transferring heat generated within the gantry from the first coolant passage to the HVAC and/or domestic water heating system.

6. The cooling system of claim 1, further comprising a fluid-to-fluid heat exchanger coupled to the fluid coolant conduit, interposed between the first and second coolant passages, with a first fluid circulating in a first coolant conduit subloop between the heat exchanger and the first coolant passage, and a second fluid circulating in a second coolant conduit subloop between the heat exchanger and the second coolant passage.

7. The cooling system of claim 1, further comprising an air-to-fluid heat exchanger within the gantry, coupled to the first coolant passage, for transfer of heat generated in ambient air within the gantry to the coolant fluid in the first coolant passage.

8. The cooling system of claim 1, the first coolant passage further comprising at least one gantry coolant loop, the gantry coolant loop oriented within the gantry and/or embedded within a radiation detector, and/or enveloping electronics modules in the gantry.

9. The cooling system of claim 1, further comprising a circulating pump for circulating the coolant fluid, a temperature sensor in the gantry, and a thermal controller coupled to the temperature sensor and the circulating pump, for selectively varying flow rate of the coolant fluid at least partially in response to gantry temperature sensed by the temperature sensor.

10. A method for cooling a gantry of a diagnostic medical imaging apparatus, comprising:
    orienting a medical imaging apparatus in an imaging room of a building structure, the medical imaging apparatus having a gantry, which includes therein at least one electromagnetic radiation detector and a first coolant passage for absorption of heat generated within the gantry;
    orienting external the gantry a solid material heatsink, having a thermal mass that receives and absorbs all heat generated within the gantry, the heatsink defining a second coolant passage;
    coupling the first and second coolant passages, in at least one closed fluid loop, with a coolant fluid conduit; and
    circulating coolant fluid within the coolant fluid conduit, for transferring heat generated within the gantry from the first coolant passage to the second coolant passage defined within the heatsink, the second coolant passage transferring the gantry heat from the coolant fluid to the heatsink by thermal conduction.

11. The method for cooling of claim 10, further comprising integrating the solid material heatsink into a structural element defining a wall or a floor or a ceiling of the building structure or buried underground, embedding the second coolant passage in said structural element.

12. The method for cooling of claim 11, further comprising heating the building structure and/or domestic hot water supply of the building structure with gantry heat that was absorbed by the heatsink.

13. The method for cooling of claim 10, further comprising forming the solid material heatsink into a modular building panel, embedding the second coolant passage therein, and incorporating the modular building panel as a structural element defining a wall or a floor or a ceiling of the building structure or buried underground.

14. The method for cooling of claim 13, further comprising heating the building structure and/or domestic hot water supply of the building structure with gantry heat that was absorbed by the heatsink.

15. The method of claim 10, further comprising:
    monitoring temperature of the detector with a temperature sensor;
    circulating the coolant fluid in the coolant fluid conduit with a variable flow-rate pump; and selectively varying coolant fluid flow rate of the pump with a thermal controller coupled to the pump and to the temperature sensor, the thermal controller varying flow rate of the pump in response to temperature of the detector.

16. The method for cooling of claim 15, further comprising conducting a plurality of medical imaging scans with the medical imaging apparatus, and selectively varying coolant fluid flow rate with the thermal controller, so that temperature fluctuations within the detectors do not vary by more than one degree Celsius (1.0° C.) during any one imaging scan and that temperature of detectors does not vary by more than six degrees Celsius (6.0° C.) during all of the plurality of imaging scans.

17. The method for cooling of claim 15, further comprising conducting a plurality of medical imaging scans with the medical imaging apparatus, and selectively varying coolant fluid flow rate with the thermal controller, so that temperature fluctuations within the detectors do not vary by more than one-half degree Celsius (0.5° C.) during any one imaging scan and that temperature of detectors does not vary by more than two degrees Celsius (2.0° C.) during all of the plurality of imaging scans.

\* \* \* \* \*